(12) United States Patent
Sveinsson

(10) Patent No.: US 9,585,940 B2
(45) Date of Patent: Mar. 7, 2017

(54) USE OF CGRP ANTAGONIST COMPOUNDS FOR TREATMENT OF PSORIASIS

(71) Applicant: Birkir Sveinsson, Bessastadahreppur (IS)

(72) Inventor: Birkir Sveinsson, Bessastadahreppur (IS)

(73) Assignee: Birkir Sveinsson, Bessastadahreppur (IS)

( * ) Notice: Subject to any disclaimer, the term of this patent is extended or adjusted under 35 U.S.C. 154(b) by 285 days.

(21) Appl. No.: 13/969,288

(22) Filed: Aug. 16, 2013

(65) Prior Publication Data

US 2014/0220030 A1 Aug. 7, 2014

Related U.S. Application Data

(63) Continuation of application No. 13/039,075, filed on Mar. 2, 2011, which is a continuation of application No. 10/524,104, filed as application No. PCT/IS03/00023 on Aug. 12, 2003, now abandoned.

(30) Foreign Application Priority Data

Aug. 12, 2002 (IS) .............................. 6496

(51) Int. Cl.
| | |
|---|---|
| *A61K 38/22* | (2006.01) |
| *A61K 31/00* | (2006.01) |
| *A61K 31/166* | (2006.01) |
| *A61K 31/517* | (2006.01) |
| *A61K 31/727* | (2006.01) |
| *A61K 38/48* | (2006.01) |
| *G01N 33/50* | (2006.01) |
| *G01N 33/74* | (2006.01) |
| *A61K 31/506* | (2006.01) |
| *C07K 16/26* | (2006.01) |
| *G01N 33/566* | (2006.01) |

(52) U.S. Cl.
CPC ............ *A61K 38/225* (2013.01); *A61K 31/00* (2013.01); *A61K 31/166* (2013.01); *A61K 31/506* (2013.01); *A61K 31/517* (2013.01); *A61K 31/727* (2013.01); *A61K 38/482* (2013.01); *C07K 16/26* (2013.01); *G01N 33/502* (2013.01); *G01N 33/5008* (2013.01); *G01N 33/5044* (2013.01); *G01N 33/5088* (2013.01); *G01N 33/566* (2013.01); *G01N 33/74* (2013.01); *G01N 2333/5753* (2013.01)

(58) Field of Classification Search
None
See application file for complete search history.

(56) References Cited

U.S. PATENT DOCUMENTS

| | | | |
|---|---|---|---|
| 5,851,556 A | 12/1998 | Breton et al. | |
| 5,932,215 A | 8/1999 | De Lacharriere et al. | |
| 5,935,586 A | 8/1999 | De Lacharriere et al. | |
| 6,019,967 A | 2/2000 | Breton et al. | |
| 6,214,816 B1 | 4/2001 | Hohlweg et al. | |
| 6,313,097 B1 | 11/2001 | Eberlein et al. | |
| 2003/0185824 A1 | 10/2003 | Vaishnaw et al. | |

FOREIGN PATENT DOCUMENTS

| | | |
|---|---|---|
| WO | WO 98/09630 A1 | 3/1998 |
| WO | WO 98/56779 | 12/1998 |
| WO | WO 00/18764 A1 | 4/2000 |

OTHER PUBLICATIONS

Rook/Wilkinson/Ebling textbook, "Textbook of Dermatology", R.H. Champion, J.L. Burton & F.J.G. Ebling, Eds., Fifth Edition, *Blackwell Scientific Publications*, 1992, p. 617 and Chapter 31, p. 1391.
Burgess et al., *J Cell Biol*. 111:2129-2138, 1990.
Claudy, A., *Path Biiol*, vol. 44, No. 10, 1996, pp. 888-894, "Les Neuromediateurs En Dermatologie. Perspecitives Therapeutiques".
Dewing S.B., Arch Dermatol. Aug. 1971; 104(2): 220-1.
Farber E.M , Lanigan S.W., Boer J., Int. J. Dermatol. Jul.-Aug. 1990; 29(6):418-20.
Farber E.M,. Ravchauduri S.P., Int. J. Dermatol. 1999; 38: 12-15.
Goodfield et al., British J. Dermatol. 1994, 131: 808-813.
Jan-ling He et al., *Journal of Clinical Dermatology*, vol. 31, No. 7, Jul. 5, 2002, pp. 407-409.
Jiang W.Y.. Ravchaudhuri S.P.. Farber E.M., Int. J. Dermatol. Aug. 1998; 37(8): 572-4.
Lazar et al., *Mol Cell Biol*. 8:1247-1252, 1988.
McDonald Hull S. et al. J. invest. Dermatol., 1989; 92: 782-785.
Naukkarinen A. et al., Arch. Dermatol. Res. 1993; 285: 341-346.
Naukkarinen. A. et al., J. Pathology, 1996; 180: 200-205.
Novotny et al., *ACTA Universitatis Carolinae Medica*, vol. 31, No. 3/4, 1985, pp. 243-245, "Psoriasis Treatment by Heparin".
Orrecchia,G. et al., Dermatologica, 1990; 180: 57-59.
Pincelli C. in Psoriasis 3rd ed. 1998, ed.: Roenikg, H.H.; Maibach H.I., Marcel Dekker Inv. NY (pp. 393-397).
Ravchauduri S.P.. Farber E.M. J. Am. Acad. Dermatol. 1993; 28(3):488-9.
Ravchauduri S.P.. Farber E.M., in Psoriasis 3rd ed. 1998, ed.: Roenikg, H.H.; Maibach H.I., Marcel Dekker Inv. NY (pp. 383-391; review).
Wu D. et al., Biochem. Soc. Trans. Aug. 2002; 30(4):468-73. Review.
Yanling, He et al., *Chin Med J.*, vol. 113, No. 8, 2000, pp. 747-751, "Calcitonin Gene-Related Peptide in Langerhans Cells in Psoriatic Plaque Lesions".
(MedlinePlus Medical Encyclopedia, [online]. Update date: Nov. 22, 2011. U.S. National Library of Medicine, NIH. [retrieved on Sep. 21, 2012]. Retrieved from the Internet: < URL:http://www.nlm.nih.gov/medlineplus/ency/article/000434.htm>. Psoriasis. see pp. 1-5).

*Primary Examiner* — Sharon Wen
(74) *Attorney, Agent, or Firm* — Thompson Hine LLP

(57) ABSTRACT

The invention provides methods and compositions for treating, preventing and/or remedying psoriasis, based on compounds that have a calcitonin-related gene peptide (CGRP) antagonistic effect. Methods are also disclosed for identifying compounds with CGRP antagonist activity which thereby are suitable candidate compounds for treating psoriasis.

1 Claim, 7 Drawing Sheets

SEQUENCE LISTING

<160> NUMBER OF SEQ ID NOS: 1

<210> SEQ ID NO 1
<211> LENGTH: 29
<212> TYPE: PRT
<213> ORGANISM: Artificial Sequence
<220> FEATURE:
<223> OTHER INFORMATION: Synthetic peptide

<400> SEQUENCE: 1

Thr His Arg Leu Ala Gly Leu Leu Ser Arg Ser Gly Gly Met Val Lys
1               5                   10                  15

Ser Asn Phe Val Pro Thr Asn Val Gly Ser Lys Ala Phe
            20                  25

USE OF CGRP ANTAGONIST COMPOUNDS FOR TREATMENT OF PSORIASIS

FIELD OF THE INVENTION

This invention relates to compositions and compounds that are CGRP antagonists, or reduces its activity for use in particular for treating and or preventing psoriasis.

BACKGROUND

Psoriasis is a chronic skin disorder that afflicts about 2 percent of the population. The disease is associated with the rapid turnover of skin cells (hyperproliferation) accompanied by a loss of differentiation so that silvery white scales form on the surface of the skin. Additionally, the capillaries become tortuous and dilated and an inflammatory reaction occurs, so that the skin reddens. The elevated silvery white scales on a contrasting red background produce the unsightly lesions characteristic of psoriasis. Psoriasis most commonly appears on the scalp, knees, elbows, hands and feet, but can affect any part of the skin. The cause of the disease is unknown, though it is believed to have a genetic component, and it has been suggested to be a T-cell mediated autoimmune skin disorder. There have been many attempts to treat the disease, and several topical and systemic treatments for psoriasis which inhibit cell division have been tried, with limited success in clearing the skin for short periods of time. Yet, the reason why these treatments work is not yet clearly understood. Treatments which have been suggested in the art appear to be symptomatic and palliative. Lesions may disappear spontaneously or as a result of the therapy, but recurrences are likely.

The present invention is directed to methods of treatment of psoriasis based on observations and, new findings that strongly indicate that psoriasis is a disease of the nervous system, and that the neuropeptide calcitonin gene-related peptide (CGRP) is a major mediator of the disease.

CGRP is a 37 amino acid polypeptide that is stored and released from nerve terminals in both the central nervous system and the peripheral nervous system. CGRP has been detected in nerves innervating the heart, peripheral and cerebral blood vessels, and kidneys by immunohisto-chemical (such as ELISA) and radioimmunoassay methods. CGRP has been shown to mediate its biological response by binding to specific cell surface receptors that have been identified in a variety of tissues.

CGRP also is a very important neuropeptide (NP) in wound healing and is the first NP that is released during that process. CGRP is a very strong vasodilator and is a strong inhibitor of delayed type hypersensitivity (DTH). CGRP is known to play a role in the regulation of hair growth, and can stimulate the proliferation of keratinocytes.

Tryptase is a protease enzyme that cleaves CGRP and reduces its activity. CGRP 8-37 is an endogen peptide that is made from CGRP by specific cleavage by tryptase. CGRP 8-37 is a high affinity antagonist for the CGRP receptor. It is thought that this antagonist is an endogen compound used by the body for the down-regulating neural signals (negative feedback control).

More capillary loops are seen in papillary dermis in psoriasis than healthy skin. These vessels in the horizontal plexus are an integral component of the lesions in psoriasis vulgaris and pustular psoriasis of von Zumbusch. The capillary loops in the papillary dermis of psoriatic lesions become dilated and tortuous before epidermal hyperplasia has been detected morphologically.

Based upon light microscopic studies of developing psoriatic lesions, Pinkus and Mehthregan have concluded that initial vasodilatation accompanied by an exudation of inflammatory cells and serum in the papilla is the initiating event in psoriasis (Pinkus, Mehthregan *J. Invest. Dermatol.* 1966 January; 46(1):109-16).

Several investigators, who studied developing 1-mm psoriatic lesions, found an upward proliferation of the dermal papillae at edges of psoriatic lesions. They believed this enlargement was one of the initiating events, although the stimulus was unknown (see e.g. Braun Falco and Cristophers, *Arch. Dermatol Forsch.* 1974:251(2):95-110). Braverman et al. found based upon the pattern by which the loops in psoriasis vulgaris return to normal and the pattern of vascular labeling in Zumbuch disease, the mechanism how the capillary loop develops. The endothelial cells in the extrapapillary venous limb enlarges and the arterial part becomes shorter as the papilla enlarges. The venous part becomes fenestrated (Braverman, I. M., in *Psoriasis* 3rd ed. (pp. 399-407), 1998, ed.: Roenikg, H. H.; Maibach H. I., Marcel Dekker Inc., NY).

An analogous phenomenon develops in the microvasculature of rat skin during the hair growth cycle (Sholley and Cotran *Am. J. Anat.* 1976 October; 147(2):243-54). The capillary network around actively growing follicle (anagen phase) increases in size by endothelial cell proliferation. Virtually all the endothelial cells are supplied by the capillaries. In human skin, both glabrous (Braverman, I. M. supra) and scalp (McLeod, W. A.; *J. Invest. Dermatol.*, 1970, 55(5), 354-7), the capillary network around the hair follicles has a venous ultrastructure: bridge fenestration and a laminated basal membrane. When the rat hair follicle enters catagen, the vascular network is greatly reduced in size, partly through loss and partly through collapse.

The growth cycle of hair is a well-known phenomenon (see e.g. *Hair Structure and LifeCycle*, http://follicle.com). Hair follicles grow in repeated cycles. One cycle can be broken down into three phases: anagen (growth phase), catagen (transitional phase), and telogen (resting phase). In any one time, about 85% of hairs of all hairs are in anagen phase. At the end of anagen phase the hairs enter into catagen phase, which lasts about one or two weeks. The telogen phase follows the catagen phase and normally lasts about 5-6 weeks. Approximately 10-15% of all hairs are in this phase at any one time. The reason why such a relatively large fraction of hairs are in telogen phase can be that they are thus prepared to act in keratinocyte proliferation in case of wound healing. To do so, a common factor will have to act in the regulation of early wound healing and regulation of the hair growth cycle. CGRP provides this role.

It is here postulated that CGRP turns hair follicles to proliferative phase to bring stem cell keratinocytes to the surface to participate in keratinocyte proliferation of the epidermis when the skin is healing. The keratinocytes come from the outer root sheath or the papilla dermis of the hair follicle. This is further supported by the fact that neuropeptides are thought to play a major role in regulating hair growth (see, e.g., *J. Invest. Dermatol. Symp. Proc.* 1997; 2(1), 61-68).

Studies have shown that the dermal papilla is probably the primary target in alopecia greata (AA). This is why CGRP is a common actor on these stem cells both in AA and psoriasis. Psoriatic keratinocytes which are all of a specific subtype are thought to come from the stem cells located in the hair follicle.

As described in the accompanying Example 4, it has been observed that psoriasis frequently appears with a hexagonal structure in the skin, that is, the psoriasis lesions appear as hexagons, both as singly isolated and also interconnected in a honeycomb pattern. It is postulated herein that these hexagons may represent neurological units of sensory innervation. This may indicate that one or more neural segments or units are involved when psoriasis lesions develop. There is a similarity in distribution and shape of Herpes Zoster (Viral nerve infection) lesions (see Example 5). This further supports the theory that the pattern of psoriasis is indicative to neural origin of the disease.

Six-corner (hexagonal) shape lesions in psoriasis are for the most part of fixed size for a given part of the body, as shown in Example 4. The exact structure of the nerve innervations in the skin has never been described in detail but the hexagonal shape is widely seen in nature as in the bee cube and in the portal system of the liver.

The most common localizations of psoriasis lesions can be explained based on neural origin of psoriasis. Striking symmetry of the lesions is common and lesions are located in areas that are known or likely nerve overlap areas, as e.g. the navel, lower back, temporal scalp region, elbows and knees. On the scalp and on the sacral area are very likely embryonic parts of the neural crest that are the last to close in the fetal development of the skin. This is further supported by the fact that aplasia cutis absence of skin most often is located on the scalp in the right temporal area, and spina bifida is located in the lumbosacral area. Location of psoriasis in the scalp, lumbosacral area, elbows and knees are particularly interesting. If one thinks of an animal on four legs, these parts are the rear, the front, and the prominent part of the extremities. Psoriasis lesions often appear at the same spots on the skin repeatedly, i.e. with a memory effect. This is the same as often seen in herpes simplex infections (viral nerve infection in peripheral skin). I have seen clinical case of a psoriasis patient that had psoriasis lesions distributed along a dermatome (nerve innervation area). The same pattern is seen in Herpes Zoster infection (viral nerve infection).

It has been observed by the Inventor that psoriasis lesions can be distributed over nerve innervation area on the hands.

Individual keratinocytes in the skin also have hexagonal form. Psoriatic keratinocytes express high levels of NGF (nerve growth factor) which stimulates growth of nerves in the skin. (*Acta Derm Ven* March 1998.84-86). Reports of psoriasis getting better after sensory nerve damage is further clinical evidence supporting the role of nerves in the pathogenesis of psoriasis. (*J. of the Am. Acad. Dermatol.* 28, 3, 488-489; *Int. J. Dermatol.* 1990; 9:418-20).

Several other observations support the thesis underlying the current Invention, that psoriasis is a neurogenerative disease, though this has not been clearly indicated in the prior art. Psoriasis developed contra lateral to hemi paresis following cerebrovascular accident. (*Int. J. Dermatol.* 3 (8): 598-9 1993 August). Patients with leprosy have destruction of peripheral nerves. It has also been noted that leprosy patients have decreased incidence of psoriasis. CGRP increases with neural trauma. CGRP 8-37 (a CGRP antagonist, described below) blocks its increase (*Am. J. Physiol.* 268 (2pt2) H584-90 1995 February). Prompt remission of a psoriatic plaque has been reported following cutaneous nerve sectioning. (Dewing, S. B. *Arch Dermatol* 104:220-221 1971).

In an investigation by means of fluorescein angiography, the retinal pigment epithelial cells in pigmented rabbits were observed. A hexagonal pattern was regularly seen away from the medullar rays. The pattern became larger at the periphery than in the posterior pole. These angiographic findings closely matched those of retinal pigment epithelial cells as seen by scanning electron microscopy and fluorescein light microscopy in sizes and shapes. This pattern in the sensory innervation in the retina is similar to that described herein for neural units of the skin. The hexagonal pattern in the skin becomes larger in the periphery, i.e. on the extremities. (Iida et al. *Nippon-Ganka Gakkai Zasshi* 1991, 95(5):421-7) CGRP and Substance P(SP) in Psoriasis and Possible Coordination in Nerve Function.

Farber et al. first proposed in 1986 a possible role for neuropeptides in the pathogenesis of poriasis (see review in Raychaudhuri, P., Farber, E. M. in *Psoriasis* 3rd ed. (pp. 383-391), 1998, ed.: Roenikg, H. H.; Maibach H. I., Marcel Dekker Inc., NY. Researchers have focused in particular on SP, and some SP antagonists have been suggested for treating psoriasis, e.g. Somatostatin and Spantide (Farber at al., supra). Both SP and CGRP are often located in the same nerves in the skin. SP and CGRP are both active in wound healing, CGRP in the early phase and SP later. Reports show high density of SP and CGRP in psoriasis skin, see e.g. Jiang et al. *Int. J. Dermatol.* 1998, 37, 572-574.

The substance P antagonist Spantide inhibits immediate and delayed type cutaneous hypersensitivity (DTH) reaction. This could be mediated through CGRP as it is known that CGRP suppresses DTH, thus SP might act as a regulator for CGRP. (Wallengren J. *Br. J. Dermatol.*, 1991, 124(4): 324-8)

Substance P regulates the vasodilator activity of CGRP. Experiments in animals revealed that this phenomenon is dependent on proteases from mast cells. (Brain S. D.; Williams, T. J. "Substance P regulates the vasodilator activity of CGRP" *Nature* 1988 335(6185), 73-5). These experiments showed that SP converts the long lasting vasodilatation induced by CGRP into a transient response when these neuropeptides were injected into human skin. A subsequent study (*J. Geronol.: Biol. Sciences* 1996; Vol. 51A, no, B354-B361) used a "blister model in the rat hind footpad" to demonstrate the ability of SP to terminate an existing vasodilator response to CGRP. The results are seen as not only confirming that combined administration of SP and CGRP in human skin can limit the vasodilator activity of CGRP, but also that a modulator inhibitory effect exerted by SP on the vasodilator activity is dose-dependent. This statement could indicate that SP changes in psoriasis are mainly of regulatory (secondary) nature.

Reports by Haukkarinen et al. (Haukkarinen et al. *Journal of Pathology*, (1996) 180, 200-205) describe studies of contact values between sensory nerves containing SP, CGRP, and VIP, and mast cells containing active tryptase and inactive chymase. The contact values of SP and CGRP with mast cells are increased in psoriatic lesions, whereas contact values for VIP are decreased. Tryptase effectively cleaves CGRP as well as VIP but not SP, whereas chymase cleaves SP. This points to a controlling mechanism in psoriasis acting to increasing cleavage of CGRP but not SP, i.e. active tryptase is increased in order to try to down-regulate CGRP, but active chymase is not increased.

I believe that in psoriasis, reduced tryptase activity may be the key step in increasing CGRP activity. This is possibly because a specific step in down-regulation (negative feedback) of CGRP is missing, because CGRP 8-37 is not being produced sufficiently. This modified peptide is a high-affinity antagonist to the CGRP receptor, as discussed above. If a specific tryptase in psoriasis is not correctly built and disfunctional, it can have substantial influence on CPGRP activity. Several mutations in genes coding for tryptase can be responsible for this. Differing severity of psoriasis can be explained by different mutations in the specific tryptase. Thus, if this is the case, psoriasis can be explained by an alteration in one enzyme system, and possibly just by alteration in a single amino acid for any given subtype of psoriasis, in the enzyme tryptase. Certain observations support this notion, for example, smoking is known to increase likelihood of psoriasis, and smoking is also known to cause defects in tryptase in lungs. This would, however, not change the effect of the present invention, that by blocking CGRP, psoriasis may be treated or prevented. This hypothesis could be readily verified by screening tryptase (or the gene coding for tryptase) from psoriasis patients and control groups to identify possible gene defects.

Several other factors point to CGRP being a much more likely mediator in psoriasis than SP. CGRP does not induce itch but SP does, and itch is most often not a symptom associated with psoriasis; CGRP does not produce weal and flare as much as SP, and SP is very active in conducting pain and burning sensation, neither of which are normally symptoms of psoriasis. CGRP however produces prolonged erythema, which is associated with psoriasis, but SP does not.

Guttae psoriasis is often seen following streptococcal infection. Several groups of streptococci can induce this. These bacteria have in common that they all produce exotoxin C, a pyrotoxin that induces vasodilatation when injected into the skin. This was used in the past as a diagnostic test of streptococcal infection known as the Dicks test. Experimental work from Beijing Medical University has shown that rats that are given endotoxin have increased level of CGRP in plasma (Tang et al. *Sheng Li Xue Bao* 1997 April; 49(2):160-6 (Medline abstract PMID: 9812851)).

CGRP is released from sensory neurones and also is the transcription of CGRP mRNA and synthesis of CGRP, in sensory neurones increased during the development of endotoxicosis in the rat. Repeated injections of endotoxin from staphylococcus induced hyperkeratosis in immunodeficiency mice. The onset of psoriasis in the wake of streptococcal infection can thus be explained by an increase in CGRP.

All the aforementioned facts and described observations strongly indicate that CGRP is a key mediator in psoriasis, which has subsequently inspired the current invention that relates to methods of treatment for psoriasis based on the use of specific CGRP antagonists.

Several compounds have been found to selectively inhibit the CGRP receptor, such as small molecular non-peptide compounds, peptides and antibodies. Such active CGRP antagonists are expected to be useful in the treatment of a variety of disease states that are mediated by CGRP. Diseases that such treatment has been suggested for include headaches, esp. migraines; NIDDM; neurogenic inflammation; cardiovascular disorders; chronic inflammation; pain; endotoxic shock; arthritis; allergic rhinitis; allergic contact dermatitis; inflammatory skin conditions; and asthma. Such compounds however, have not to my knowledge been suggested for treatment of psoriasis.

Compounds disclosed in the prior art found to be useful as antagonists of CGRP include 4-sulfinyl benzamide compounds (WO 98/56779), 3,4-dinitrobenzamide compounds (WO 98/09630), a group of modified amino acids (WO 00/55154), and benzamidazolinyl piperadine compounds (WO 00/18764).

Antibodies against CGRP have also been described, and inactive derivatives of CGRP, e.g. CGRP 8-37 which differs from normal CGRP in that it lacks 8 N-terminal amino acids. U.S. Pat. No. 5,935,586 describes the use of CGRP antagonists in therapeutic/cosmetic compositions for treating diseases of the skin, in particular, lichens, prurigos, pruriginous toxidermas and severe pruritus. U.S. Pat. No. 5,932,215 describes similar use for treating skin redness, rosacea and discrete erythema.

SUMMARY OF THE INVENTION

The hypothesis of the present invention suggests that overrepresentation of calcitonin gene related peptide (CGRP) is responsible for most of the pathological phenomena of psoriasis like hyperproliferation, increased number of T-cells, increased blood flow, and localization of lesions. It can also explain the therapeutic effect of sunlight, and the negative effect of streptococcal infection on psoriasis. Alopecia greata (AA) is a functional hair disease where a lack of CGRP seems to be a causing factor. An inverse relationship between AA and psoriasis has been observed and is described herein. CGRP can be a common factor in both diseases, as it is involved in the use of papillary cells for wound healing and through that route can activate hair follicles in the wound healing process. It is known that psoriasis is a disease connected to the early wound healing process. The observations described herein showing hexagonal structure of psoriasis lesions strongly suggests that the disease involves neural units of sensory innervation. In conclusion, it is a novel hypothesis of the Inventor set forth and supported herein that psoriasis is a disease of neural origin and CGRP is likely to be a key mediator of the disease. According to this hypothesis, it is the regulation of CGRP that is not functioning properly in psoriasis, and consequently, regulation of CGRP by use of a CGRP antagonistic compound is a way of controlling psoriasis.

The present invention describes a novel method for the treatment and prevention of psoriasis by modulating the concentration of CGRP in the body, especially in the skin, e.g., by the use of CGRP antagonists. The invention is supported by the novel observations and descriptions herein that explain psoriasis as a disease of neurological origin for which CGRP s a key mediator.

The invention is based on the notion that by changing the level of CGRP, at least in the psoriatic lesions, such as by blocking the activity of CGRP, the disease can be treated and/or prevented. This may effected by the administration of CGRP antagonist compounds, or by administering tryptase or other compounds affecting the level of CGRP.

DETAILED DESCRIPTION

As mentioned, the current invention relates to methods for treating, remedying or preventing psoriasis by the use of CGRP antagonist compounds. To date it has not been envisaged to treat psoriasis with CGRP antagonists. Accordingly, the present invention features the use of at least one CGRP antagonist compound for the treatment of psoriasis.

'CGRP antagonist' in this context represents any molecule, whether organic or inorganic, which is capable of reducing the level of active CGRP, e.g., by effecting inhibition of the receptor binding of CGRP or of effecting inhibition of the synthesis and/or release of CGRP by nerve fibers, or enhancing the breakdown of active CGRP. Thus tryptase active polypeptides falls within this category as defined herein as they can affect the level of CGRP by cleavage of the peptide, as well as compounds stabilizing tryptase, such as heparin. As mentioned above, many compounds have been recently developed that fulfill these criteria and thus are useful in the current invention.

Treatment in this context indicates any form of therapy that cures or relieves at least partially the symptoms of the disease, for at least a period of time, remedying the disease indicates herein full or partial relief of psoriasis symptoms.

Microdialysis is a method for tissue fluid sampling. It has been used both in the skin and other tissues.

Laser-Doppler flow measurement is a technique for measuring localized superficial blood flow in the skin.

In a first aspect, the invention provides a method of treating psoriasis in a subject comprising administering to the subject a therapeutically effective dose of at least one CGRP antagonist compound in a pharmaceutically acceptable formulation. A therapeutically effective dose will depend on the particular compound selected but is typically in the range of about 0.00001% to 5% of the total weight of a pharmaceutical composition being used for said treatment, preferably in the range of about 0.0001% to 2.5% of weight, such as in the range of 0.001 to 1% of weight, or in the range of 0.001 to 0.1% of weight.

A suitable pharmaceutically acceptable formulation may be formulated according to conventional pharmaceutical methods, depending on the compound being selected and the intended route of administration, as discussed further below.

The method according to the invention includes both systemic and/or local treatment. Accordingly, the compositions for use according to the invention may be administered orally, nasally, rectally, pulmonary, buccally or via subcutaneous, intravenous or intramuscular injection in order to reach the lesions from a distal administration, or by administering the composition locally, such as topically, dermally, intradermal or subcutaneously, or via dermal or subcutaneous infusion such as through microdialysis. However, presently preferred embodiments comprise topical administration.

It will thus be readily understood from the description herein, that the invention provides in a related aspect, the use of a CGRP antagonist compound for the manufacture of a medicament for treating, remedying or preventing psoriasis in a subject in need thereof. Such medicaments are preferably such compositions as are disclosed herein.

However, in another aspect, the invention provides a method to reduce hair growth by the application of a CGRP antagonist compound such as defined above. This aspect stems from the novel theory that CGRP regulates the hair growth cycle, as discussed above. In preferred embodiments of the invention, these methods comprise the topical or dermal application of medicaments such as a cream, ointment, gel, paste, iontopophoresis system, liquid or lotion, to the area where hair growth reducing effect is wanted.

The topical formulations according to the invention comprise an active ingredient together with one or more pharmaceutically acceptable carrier and/or excipient compounds and optionally one or more therapeutically active ingredient.

Formulations suitable for topical administration may be formulated into any pharmaceutical form normally employed for such an application, these include liquid or semi-liquid preparations including lotions, creams, pastes, ointments, liposomes, gels, such as for iontopophoresis, suspensions and emulsions, including oil/water (w/o), w/o, o/w/o, w/o/w emulsions or microemulsions. They may suitably be obtained by mixing the active ingredient in finely-divided or powdered form, alone or in solution or suspension in an aqueous or non-aqueous fluid, with the aid of suitable machinery, with a hydrophobic or hydrophilic basis. The basis may comprise hydrocarbons such as hard, soft or liquid paraffin, glycerol, waxes (e.g., beeswax, carnauba wax), metallic soap, a mucilage, an oil of natural origin such as corn, almond, castor, or olive oil, mineral oils, animal oils (perhydroxysqualene); or a fatty acid such as stearic or oleic together with an alcohol such as ethanol, isopropanol, and propylene glycol. The formulation may include any suitable surface active agent such as an anionic, cationic, or non-ionic surfactant such as sorbitan esters or polyoxyethylene derivatives thereof. Suspending agents such as natural gums; cellulose derivatives or inorganic materials such as silicaceous silicas may also be included. The formulations may additionally comprise absorbtion promoters, stabilizers, e.g. protein stabilizing agents, known in the art.

Known CGRP antagonist compounds which are useful in the current invention include 4-sulfinyl benzamide compounds such as those disclosed in WO 98/56779, 3,4-dinitrobenzamide compounds such as those disclosed in WO 98/09630, benzamidazolinyl piperadine compounds such as disclosed in WO 00/18764, CGRP derivatives including CGRP 8-37, having the sequence THRLAGLLSRSGGM-VKSNFVPTNVGSKAF (SEQ ID NO:1), and anti-CGRP antibodies. An interesting compound described in the art a non-peptide molecule produced by Boehringer Ingelheim, termed BIBN4096BS (see, Wu et al., *Biochem. Soc. Trans.* 2002, August 30(4): 468-473).

Compounds that are believed to have a CGRP antagonist activity and thus being candidate compounds for use according to the present invention include:

(±)-4-[(2-chlorophenyl)sulfinyl]-N-methyl-N-(2-methylphenyl)-3-nitrobenzamide;

(+)-4-[(2-chlorophenyl)sulfinyl]-N-methyl-N-(2-methylphenyl)-3-nitrobenzamide;

(−)-4-[(2-chlorophenyl)sulfinyl]-N-methyl-N-(2-methylphenyl)-3-nitrobenzamide;

(±)-4-[(4-chlorophenyl)sulfinyl]-N-methyl-N-(2-methylphenyl)-3-nitrobenzamide;

(±)—N-methyl-N-(2-methylphenyl)-4-[(1-oxido-2-pyridinyl)sulfinyl]-3-nitrobenzamide;

(±)—N-methyl-N-(2-methylphenyl)-3-nitro-4-(2-thiazolylsulfinyl)benzamide;

(±)—N-methyl-N-(2-methylphenyl)-4-[(5-methyl-1,3,4-thiadiazol-2-yl)sulfinyl]-3-nitrobenzamide;

N-[3-[(diethylamino)carbonyl]propyl]-N-(-2-ethylphenyl)-3-nitro-4-(2-thiazolylsulfinyl)benzamide;

1-[4-amino-3,5-dibromo-N-[[4-(3,4-dihydro-2(1H)-oxoquinazolin-3-yl)-1-piperidinyl]methylsulfonyliminomethyl]-D-phenylalanyl]-4-(1-piperidinyl)-piperidine, 1-[4-amino-3,5-dibromo-N-[[4-(3,4-dihydro-2(1H)-oxoquinazolin-3-yl)-1-piperidinyl]cyanoiminomethyl]-D-phenylalanyl]-4-(1-piperidinyl)-piperidine, 1-[4-amino-3,5-dibromo-N-[[4-(3,4-dihydro-2(1H)-oxo quinazolin-3-yl)-1-piperidinyl]phenylsulfonyliminomethyl]-D-phenylalanyl]-4-(1-piperidinyl)-piperidine, 1-[3,5-dibromo-N-[[4-(3,4-dihydro-2(1H)-oxoquinazolin-3-yl)-1-piperidinyl]cyanoiminomethyl]-D-tyrosyl]-4-(1-piperidinyl)-piperidine, 1-[$N^2$-[3,5-dibromo-N-[[4-(3,4-dihydro-2(1H)-oxoquinazolin-3-yl)-1-piperidinyl]methylsulfonyliminomethyl]-D-tyrosyl]-L-lysyl]-4-(4-pyridinyl)piperazine, 1-[$N^2$-[3,5-dibromo-N-[[4-(3,4-dihydro-2(1H)-oxoquinazolin-3-yl)-1-piperidinyl]phenylsulfonyliminomethyl]-D-tyrosyl]-L-lysyl]-4-(4-pyridinyl)piperazine, 1-[4-amino-3,5-dibromo-N-[[4-(3,4-dihydro-2(1H)-oxoquinazolin-3-yl)-1-piperidinyl]cyanoiminomethyl]-D-phenylalanyl]-4-(1-methyl-4-piperidinyl)-piperidine, 1-[4-bromo-N-[[4-(3,4-dihydro-2(1H)-oxoquinazolin-3-yl)-1-piperidinyl]cyanoiminomethyl]-3,5-dimethyl-D,L-phenylalanyl]-4-(1-piperidinyl)-piperidine, 1-[3,5-dibromo-N-[[4-(3,4-dihydro-2(1H)-oxoquinazolin-3-yl)-1-piperidinyl]cyanoiminomethyl]-D-tyrosyl]-4-(4-pyridinyl)piperazine, 1-[4-amino-3,5-dibromo-N[[4-(3,4-dihydro-2(1H)oxoquinazolin-3-yl)-1-piperidinyl]cyanoiminomethyl]-D-phenylalanyl]-4-(4-pyridinyl)piperazine, 1-[3,5-dibromo-N-[[4-(3,4-dihydro-2(1H)-oxoquinazolin-3-yl)-1-piperidinyl]cyanoiminomethyl]D-tyrosyl]-4-(1-methyl-4-piperidinyl)-piperidine, 1-[3,5-dibromo-N-[[4-[3,4-dihydro-2(1H)-oxoquinazolin-3-yl]-1-piperidinyl]cyanoiminomethyl]-D-tyrosyl]-4-(4-methyl-1-piperazinyl)piperidine, 1-[4-bromo-N-[[4-(3,4-dihydro-2(1H)-oxoquinazolin-3-yl)-1-piperidinyl]cyanoiminomethyl]-3,5-dimethyl-D,L-phenylalanyl]-4-(1-methyl-4-piperidinyl)piperidine, 1-[4-amino-3,5-dibromo-N-[[4-[1,3-dihydro-4-phenyl-2(2H)-oxoimidazol-1-yl]-1-piperidinyl]cyanoiminomethyl]-D-phenyl-alanyl]-4-(4-methyl-1-piperazinyl)piperidine, 1-[4-amino-3,5-dibromo-N-[[4-(2,3,4,5-tetrahydro-2(1H)-oxo-1,3-benzodiazepin-3-yl)-1-piperidinyl]cyanoiminomethyl]-D-phenylalanyl]-4-(4-methyl-1-piperazinyl)piperidine, 1-[4-amino-3,5-dibromo-N-[[4-(2,4-dihydro-5-phenyl-3(3H)-oxo-1,2,4-triazol-2-yl)-1-piperidinyl]cyanoiminomethyl]-D-phenylalanyl]-4-(1-piperidinyl)-piperidine, 1-[4-amino-3,5-dibromo-N-[[4-(2,3,4,5-tetrahydro-2(1H)-oxo-1,3-benzodiazepin-3-yl)-1-piperidinyl]cyanoiminomethyl]-D-phenylalanyl]-4-(1-piperidinyl)-piperidine, 1-[3,5-dibromo-N-[[4-(2,4-dihydro-5-phenyl-3(3H)-oxo-1,2,4-triazol-2-yl)-1-piperidinyl]cyanoiminomethyl]-D-tyrosyl]-4-(1-piperidinyl)-piperidine, 1-[3,5-dibromo-N-[[4-(2,3,4,5-tetrahydro-2(1H)-oxo-1,3-benzodiazepin-3-yl)-1-piperidinyl]cyanoiminomethyl]-D-tyrosyl]-4-(1-piperidinyl)-piperidine, 1-[3,5-dibromo-N-[[4-(2,4-dihydro-5-phenyl-3(3H)-oxo-1,2,4-triazol-2-yl)-1-piperidinyl]cyanoiminomethyl]-D-tyrosyl]-4-(1-methyl-4-piperidinyl)piperazine, 1-[3,5-dibromo-N-[[4-(2,3,4,5-tetrahydro-2(1H)-oxo-1,3-benzodiazepin-3-yl)-1-piperidinyl]cyanoiminomethyl]-D-tyrosyl]-4-(1-methyl-4-piperidinyl)piperazine, 1-[4-amino-3,5-dibromo-N-[[4-(2,4-dihydro-5-phenyl-3(3H)-oxo-1,2,4-triazol-2-yl)-1-piperidinyl]cyanoiminomethyl]-D-phenylalanyl]-4-(1-methyl-4-piperidinyl]piperazine, 1-[4-amino-3,5-dibromo-N-[[4-(2,3,4,5-tetrahydro-2(1H)-oxo-1,3-benzodiazepin-3-yl)-1-piperidinyl]cyanoiminomethyl]-D-phenylalanyl]-4-(1-methyl-4-piperidinyl)piperazine, 1-[3,5-dibromo-N-[[4-(3,4-dihydro-2(1H)-oxoquinazolin-3-yl)-1-piperidinyl]cyanoiminomethyl]-4-methyl-D,L-phenylalanyl]-4-(1-methyl-4-piperidinyl)-piperidine, 1-[3,5-dibromo-N-[[4-(3,4-dihydro-2(1H)-oxoquinazolin-3-yl)-1-piperidinyl]cyanoiminomethyl]-4-methyl-D,L-phenylalanyl]-4-(1-piperidinyl)-piperidine, 1-[3,5-dibromo-N-[[4-(3,4-dihydro-2(1H)-oxoquinazolin-3-yl)-1-piperidinyl]cyanoiminomethyl]-4-methyl-D,L-phenylalanyl]-4-(4-pyridinyl)piperazine, 1-[4-amino-3,5-dibromo-N-[[4-[1,3-dihydro-2(2H)-oxoimidazo[4,5-c]quinolin-3-yl]-1-piperidinyl]cyanoiminomethyl]-D-phenylalanyl]-4-(1-piperidinyl)piperidine, 1-[4-amino-3,5-dibromo-N-[[4-(7-methoxy-2,3,4,5-tetrahydro-2(1H)-oxo-1,3-benzodiazepin-3-yl)-1-piperidinyl]cyanoiminomethyl]-D-phenylalanyl]-4-(1-piperidinyl)-piperidine, 1-[4-amino-3,5-dibromo-N-[[4-(5,7-dihydro-6-oxodibenzo[d,f][1,3]-diazepin-5-yl)-1-piperidinyl]cyanoiminomethyl]-D-phenylalanyl]-4-(1-piperidinyl)-piperidine, 1-[4-amino-3,5-dibromo-N-[[4-(7-methoxy-2,3,4,5-tetrahydro-2(1H)-oxo-1,3-benzodiazepin-3-yl)-1-piperidinyl]cyanoiminomethyl]-D-phenylalanyl]-4-(1-methyl-4-piperidinyl)piperazine, 1-[4-amino-3,5-dibromo-N-[[4-[1,3-dihydro-2(2H)-oxoimidazo[4,5-c]quinolin-3-yl]-1-piperidinyl]cyanoiminomethyl]-D-phenylalanyl]-4-(1-methyl-4-piperidinyl)piperazine, 1-[4-amino-3,5-dibromo-N-[[4-(2,3,4,5-tetrahydro-2(1H)-oxo-1,3-benzodiazepin-3-yl)-1-piperidinyl]sulfonyl]-D-phenylalanyl]-4-(1-methyl-4-piperidinyl)piperazine, 1-[3,5-dibromo-N-[[4-(7-methoxy-2,3,4,5-tetrahydro-2(1H)-oxo-1,3-benzodiazepin-3-yl)-1-piperidinyl]cyanoiminomethyl]-D-tyrosyl]-4-(1-piperidinyl)piperazine, 1-[3,5-dibromo-N-[[4-(7-methoxy-2,3,4,5-tetrahydro-2(1H)-oxo-1,3-benzodiazepin-3-yl)-1-piperidinyl]cyanoiminomethyl]-D-tyrosyl]-4-(1-methyl-4-piperidinyl)piperazine, 1-[3,5-dibromo-N-[[4-[1,3-dihydro-2(2H)-oxoimidazo[4,5-c]quinolin-3-yl]-1-piperidinyl]cyanoiminomethyl]-D-tyrosyl]-4-(1-piperidinyl)piperidine, 1-[3,5-dibromo-N-[[4-[1,3-dihydro-2(2H)-oxoimidazo[4,5-c]quinolin-3-yl]-1-piperidinyl]cyanoiminomethyl]-D-tyrosyl]-4-(1-methyl-4-piperidinyl)piperazine, 1-[4-amino-3,5-dibromo-N-[[4-(7-methoxy-2,3,4,5-tetrahydro-2(1H)-oxo-1,3-benzodiazepin-3-yl)-1-piperidinyl]cyanoiminomethyl]-D-phenylalanyl]-4-(4-methyl-1-piperazinyl)-piperidine, 1-[4-amino-3,5-dibromo-N-[[4-[1,3-dihydro-2(2H)-oxoimidazo[4,5-c]quinolin-3-yl]-1-piperidinyl]cyanoiminomethyl]-D-phenylalanyl]-4-(4-methyl-1-piperazinyl)piperidine, and pharmaceutically acceptable salts thereof.

It is further contemplated that indirect inhibitors of CGRP activity may be useful according to the invention. These include the capsaicin blocker capzaezine, as CGRP is postulated to be under the influence of capsaicin through the vanillin receptor. Other such indirect inhibitors include Histamine H3-receptor agonists such as Imetit which can downregulate CGRP.

In a useful embodiment of the invention, the pharmaceutical composition comprising a CGRP antagonist compound is administered for treatment of psoriasis in combination with another treatment form, such as UVB treatment which is performed with standard methods in the art.

In another aspect of the invention, a method is provided for identifying a candidate compound for use in a medicament for treating psoriasis. The method comprises the steps of obtaining a compound suspected of binding to a CGRP receptor; adding the compound at varying concentrations such as in the range of about 0.1 μM to 1 mM to samples comprising CGRP receptors and incubating for a suitable time; adding labeled CGRP peptide to the incubated samples (e.g., radiolabeled, such as by iodine$^{125}$, though other labeling methods well known in the art are applicable as well); determining the binding of the labeled CGRP peptide to the CGRP receptor in said samples with varying concentration of the candidate compound; and determining the binding affinity of the compound to the CGRP receptor;

whereby a compound that is determined to bind the CGRP receptor is identified as a candidate compound for use in a medicament for treating psoriasis. An embodiment of the method according to the invention is described in detail in Example 10.

In one embodiment of the method said samples comprise live cells having surface bound CGRP receptors. In certain embodiments said samples comprise cell membrane preparations.

EXAMPLES

Example 1

Case Study

Possible Involvement of Neuropeptidergic Sensory Nerves in AA

A recent study by R. Rossi et al. (Rossi, R. et al. *Neuroreport*, 8, 1135-1138 1997) indicated that patients with AA have lower basal blood flow. It was further shown that CGRP and SP (substance P) levels but not VIP (vasoactive intestinal peptide) are decreased in scalp biopsies of patients affected by AA. Reaction to stimuli is altered, such that a greater and more prolonged vasodilation in response to intradermal CGRP is observed in alopecic scalp than in controls. This is suggested by the authors of the study to indicate CGRP receptor hypersensitivity, due to a previous reduction in the amount of the neuropeptide present.

Example 2

Clinical Observation of a Patient with AA and Psoriasis

Figure 1A:
FIGS. 1a and 1b: Show images that depict the scalp of a patient with *Alopecia aerata* and psoriasis.
Figure 1B:
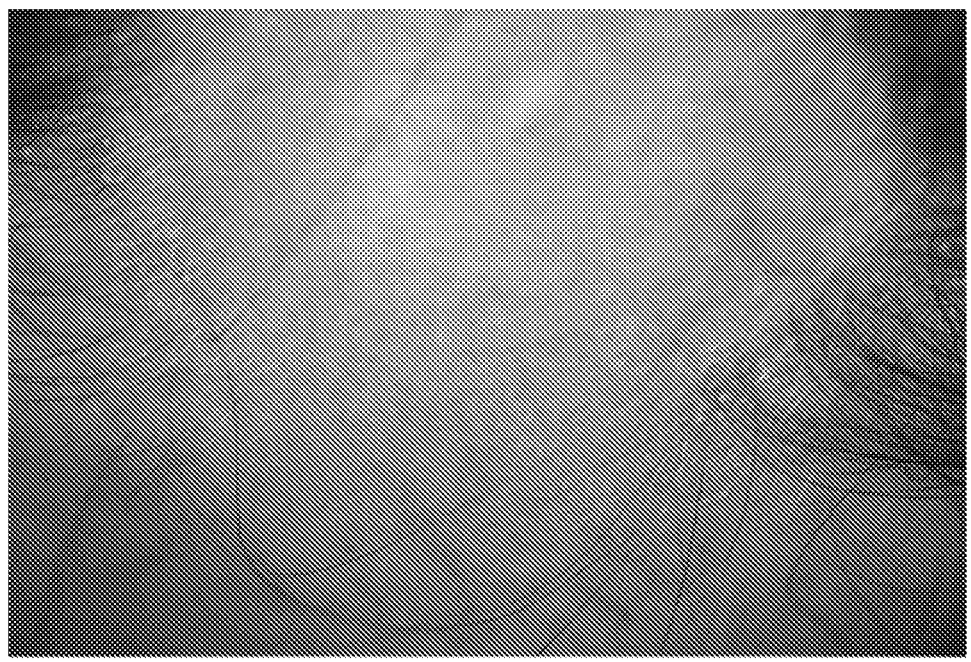

A clinical observation of a Down's syndrome patient with AA and psoriasis showed that the patient had AA covering an area from one ear to the other through his occipital region. H is whole scalp was covered with psoriasis except for the area where he had AA (see FIGS. 1a and 1b). In those areas the scalp was clinically normal. The patient had psoriasis on his elbows and a strong family history of psoriasis.

The observation strongly indicates that there is an inverse relationship between the two diseases, which has to my knowledge not been described before. In conjunction with the results of Example 1 that CGRP levels are lower in AA areas, this further supports the notion that CGRP is a causative agent in psoriasis.

Example 3

Clinical Observation of Psoriasis Patients Treated with UVB Therapy

Patients receiving UVB treatment according to standard clinical practice were observed and interviewed. It was noticed that several patients experienced transient worsening of psoriasis after their first treatment sessions, in the very first days after initiating treatment, before they begin to get better. Worsening was defined as flare-up or increased size of existing lesions or appearance of new ones.

Out of 95 patients interviewed, 38 said they had experienced worsening of their psoriasis. 21 got new lesions, most often lasting for 1 or 2 days. These lesions were often described as small, thin and red macules. 17 patients noticed a short worsening period of already existing psoriasis lesions. These symptoms were noted typically within 24-48 hours after first treatment. All patients, however, benefited from the treatment, i.e., received overall improvement of psoriasis over a longer time.

I postulate that in the beginning of the treatment, increased CGRP is a normal reaction to UV radiation and heat trauma. (This has been observed experimentally in rats, see Gillardon et al. *Neurosci. Lett.* 1991 Apr. 1; 124(2):144-7) As the stimulus is ongoing, it is conceivably beneficial for the body to increase the specific defense mechanism and decrease cell turnover, by down-regulation of CGRP. In such a way the risk of mutation and skin cancer may be reduced. Thus, the increased CGRP levels in skin during beginning of UVB therapy enhances the patient's psoriasis symptoms, before the healing effect of the therapy sets in.

Example 4

Study of Psoriasis Pattern and Location

Figure 2A:
FIGS. 2a and 2b: Show Psoriasis pattern on legs of patients.
Figure 2B:
Figure 3:
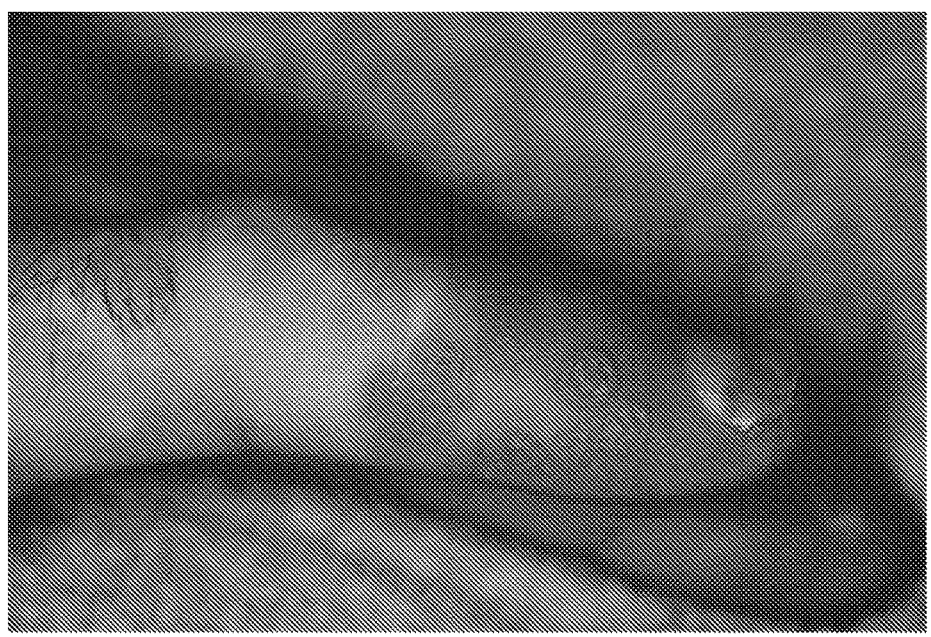
FIG. 3 Shows Psoriasis lesions on a finger.

Psoriasis lesions on a number of patients have been carefully studied to analyze patterns of the lesions. A hexagonal pattern can be observed on many patients, see FIGS. 2-3. Such pattern has not been described before. It is postulated that the pattern is a representation of neurological Example 5

Herpes Zoster Pattern

Figure 4:
FIG. 4: Is an image showing Herpes zoster lesions.

The pattern of Herpes Zoster lesions has been studied. It is noted that such patterns also show hexagonal pattern (FIG. 4). Herpes Zoster, a viral nerve infection, has a known neurological connection, and therefore the fact that hexagonal patterns are observed in both Herpes Zoster and psoriasis supports that such patterns are representations of neurological units.

Example 6

Psoriasis Lesions Formed after Skin Injury

Figure 5:
FIG. 5: Shows Psoriasis lesions formed after skin injury.

A psoriasis patient developed psoriatic lesions where his skin had been scratched or injured. It is frequently observed that lesions appear where the skin has been injured, this is called the Koebner's phenomenon. I observed that the lesions, showed a fine hexagonal pattern (see FIG. 5). It can thus be concluded that whereas the location of the "straight-line" lesions is caused by the injury to the skin, the finer structure-pattern comprising semi-circles or hexagons, is a strong indication of the disease's neural connection. It can further be observed in FIG. 5 that the sizes of the hexagons are interrelated such as e.g. the broader lines are comprised of hexagons that are comprised of the smaller hexagonal units of the finer lines. This propagation indicates that neural

Example 7

Study of Alopecia Greata Pattern

Figure 6A:
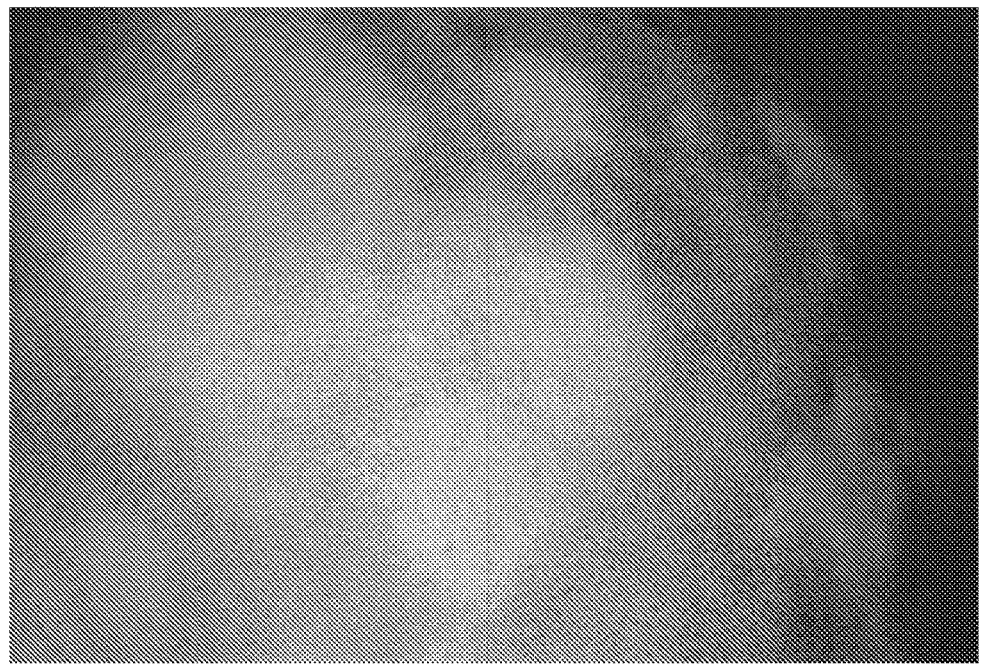
FIG. 6: Is an image showing pattern of Alopecia aerata on the skalp of a patient.
Figure 6B:

FIGS. 6a and 6b of the scalp of a patient with Alopecia greata (AA) reveals that Alopecia spots display non-circular forms resembling hexagonal shape. In light of the discussion herein regarding the relationship between AA and psoriasis, the indication that AA also shows patterns indicative of neural factors further support the notion of psoriasis being a neurological disorder.

Example 8

Case Study

Topical Immunotherapy for Alopecia areata

Orecchia et al. (Orecchia, G. et al. *Dermatologica* 1990, 180, 57-59) describe treatment of AA with SABDE (squaric acid dibutylester), a topical sensitizer. A patient who received the treatment developed psoriasis at the same spot where he got hair regrowth. Hairs on the psoriatic plaques were the last to fall off when the disease progressively worsened after treatment, to Alopecia Universalis.

As discussed in the detailed description, to activate keratinocytes from hair follicles which act as reserve cells, CGRP can turn the hair in resting phase (telogen phase) into active phase (anagen phase). When the body is exposed to antigen in very small quantities (as topical immunotherapy) CGRP is released to stop the process of delayed type hypersensitivity (DTH) to evolve. I believe that is the reason why SABDE and DPCP are effective in treatment of Alopecia Aerata. This mechanism involving CGRP as a down-regulator of DTH and actor in early wound healing which is able to turn hair follicles from telogen to anagen phase explains why there is an inverse relationship between psoriasis and AA, as demonstrated in the Example 1.

Example 9

Lotion for Treating Psoriasis

A lotion for treatment and/or prevention of psoriasis by topical administration may be prepared as follows:

A suitable compound is selected, from those disclosed in the description or a compound identified with the method of Example 10 percent lotion is prepared as follows: about 0.1 to 0.5 g of the compound is dissolved in ethanol (6 ml), and the solution is admixed with a water-in-oil lotion (95 g) prepared from mineral oil, cottonseed oil, isopropyl palmitate and water with a surfactant such as sorbitan sesquioleate. The ingredients in the water-in-oil lotion are present for example in 10:10:5:70:5 parts by weight respectively.

Example 10

Screening for Antagonistic Compounds

A method is described in WO 98/56779 to screen for compounds that hinder the CGRP receptor from binding CGRP. Thus, the method will identify compounds that are likely to be useful for the current invention.

Briefly, the selected test compounds are assayed for the inhibition of [$^{125}$I] CGRP (from Amersham, Chicago, Ill.). SK-N-MC cells (American Type Culture Collection, Rockville, Md.) are grown in Minimum Essential Medium ("MEM") containing fetal calf serum (10%). Cells are grown in T-150 flasks or Costar multiwell plates and maintained at 37° C. in a 90% humidified incubator with an atmosphere of 5% $CO_2$ and 95% air.

The cells are homogenized in 5 mM Tris-HCl pH 7:4, 10 mM Na-EDTA and the homogenate centrifuged at 48,000 g for 20 min at 4° C. The pellet is re-suspended in 20 mL Na-HEPES pH 7.4, 10 mM $MgCl_2$ and recentrifuged. The membrane pellets are re-suspended in the same buffer and stored frozen at −70° C. The protein concentration is measured by the Pierce BCA method using BSA (Bovine serum albumin) as a standard.

The [$^{125}$I]CGRP receptor binding assay is performed using a buffer of 20.mM Na-HEPES pH 7.4, 10 mM MgCl12, 0.05% BSA and 0.1 mg/mL bacitracin. The membranes (50 µg/mL) are incubated with various concentrations (such as in the range of about 1 µM and 1 mM) of the test compounds and 40 pM [$^{125}$I]CGRP in a total volume of 500 µL for 60 min at 25° C. The reaction is terminated by addition of 2 mL ice-cold 0.9% NaCl, followed by rapid filtration through Skatron Filtermates pre-soaked in 0.5% polyethylenimine (PEI). The filters are rinsed twice with 2 mL of cold 0.9% NaCl and the radioactivity counted in a gamma counter. The binding data is analyzed with conventional ligand-binding calculations and programs, such as the LIGAND 2 program.

Example 11

Measurement of CGRP in Edges Surrounding Psoriasis Lesions

Laser Doppler blood flow measurement was used to measure blood flow in normal skin surrounding psoriasis lesions to determine the location of the active edge of psoriasis lesions. It is known that psoriasis lesions grow directionally, i.e., have a growing or active edge (see, Cunliff et al. *J. Invest. Dennatol.* 1989, 92(6):782-5). CGRP levels were measured in both the active edge and the inactive (opposite) edge in two subjects having psoriasis lesions. Initial results indicate that CGRP levels are increased in the active edge as compared to the inactive edge. The experiment was conducted by the use of microdialysis equipment for tissue fluid sampling with a 15 kDa cutoff probe; both the active and inactive edge were sampled for a total of 165 min. each sample to obtain a volume of 165 µL in each sample. Neuropeptide CGRP concentration was measured with ELISA. Tissue biopsies from the sampled skin locations were taken after the tissue fluid sampling. At the active edge increased blood flow was observed indicated by increased capillary blood vessels indicated by increased number of capillary loops in the papillary dermis, which also were dilated. No epidermal hyperplasia or T-cell activation were found.

The results strongly indicate that increased concentration in CGRP level in the skin is a very early event in the development of psoriasis. This supports that failure in regulating the GCRP level (i.e. an enhanced CGRP level) could be a causative factor in the psoriasis disease.

The invention claimed is:

1. A method of systemic treatment of psoriasis in a subject in need of treatment, the method comprising subcutaneously injecting, to a localized site in the subject in need thereof, a therapeutically effective dose of CGRP 8-37 as the only active agent in a pharmaceutically acceptable formulation, the injection resulting in psoriasis treatment not localized to the site of injection.

* * * * *